United States Patent
Theodore et al.

(10) Patent No.: US 12,011,190 B2
(45) Date of Patent: Jun. 18, 2024

(54) ULTRASONIC SPINAL SURGERY METHOD AND ASSOCIATED SURGICAL INSTRUMENT

(71) Applicant: Misonix, LLC, Farmingdale, NY (US)

(72) Inventors: Nicholas Theodore, Ruxton, MD (US); Dan Voic, Cedar Grove, NJ (US); Paul Mikus, Miami, FL (US); Christopher Ballor, Chesterfield, MI (US); Sharon Klugewicz, Rockville Centre, NY (US)

(73) Assignee: Misonix, LLC, Farmingdale, NY (US)

( * ) Notice: Subject to any disclaimer, the term of this patent is extended or adjusted under 35 U.S.C. 154(b) by 459 days.

(21) Appl. No.: 17/327,041

(22) Filed: May 21, 2021

(65) Prior Publication Data
US 2022/0370094 A1 Nov. 24, 2022

(51) Int. Cl.
*A61B 17/32* (2006.01)
*A61B 17/16* (2006.01)

(52) U.S. Cl.
CPC .. *A61B 17/320092* (2013.01); *A61B 17/1659* (2013.01); *A61B 17/1671* (2013.01); *A61B 2017/320084* (2013.01); *A61B 2217/005* (2013.01); *A61B 2217/007* (2013.01)

(58) Field of Classification Search
CPC ........ A61B 17/1671; A61B 17/320068; A61B 17/320092; A61B 17/1659; A61B 2018/00339; A61B 2017/320084; A61B 2017/320073; A61B 2217/005; A61B 2217/007

See application file for complete search history.

(56) References Cited

U.S. PATENT DOCUMENTS

| 5,976,105 A * | 11/1999 | Marcove ........ A61B 17/320068 604/500 |
| 7,025,735 B2 | 4/2006 | Soring et al. |
| 2008/0058775 A1 | 3/2008 | Darien et al. |
| 2008/0234709 A1 | 9/2008 | Houser |
| 2008/0300591 A1* | 12/2008 | Darian ........... A61B 17/320068 606/41 |
| 2021/0267622 A1* | 9/2021 | Ellegala ......... A61B 17/320068 |
| 2022/0370092 A1* | 11/2022 | Voic ............... A61B 17/320068 |

FOREIGN PATENT DOCUMENTS

| EP | 2635192 B1 | 3/2019 |
| EP | 0784451 B1 | 9/2022 |

* cited by examiner

*Primary Examiner* — Ashley L Fishback
(74) *Attorney, Agent, or Firm* — Cooley LLP

(57) ABSTRACT

An elongate ultrasonic dissector-shaver probe has a laterally enlarged head extending distally and transversely from a distal end of a shaft and provided with sets of spiraling ribs. In a disc space preparation procedure, the probe is inserted into a spinal disc between two vertebral endplates, ultrasonic vibratory energy is conducted into the probe, and the probe is manipulated to move the laterally enlarged head in three spatial directions within the spinal disc to thereby disrupt and shred the spinal disc material into fragments extracted from the space, in part by suction and in part by using forceps to pull spinal disc fragments from the operative space or surgical site between the vertebral endplates.

11 Claims, 3 Drawing Sheets

ULTRASONIC SPINAL SURGERY METHOD AND ASSOCIATED SURGICAL INSTRUMENT

BACKGROUND OF THE INVENTION

This invention relates to surgical operations commonly known as discectomies and disc space preparation procedures.

The spinal column is comprised in part of bones or vertebrae and in part of fibrous discs that are disposed between the vertebrae. The discs normally function as cushions separating the vertebrae. With age, owing to a drying of the discs, the cushioning effect may be reduced. Also injury can cause a disc to bulge and press on the nerve root leaving the spinal column, possibly causing extreme pain.

More specifically, when the outer wall of a disc, called the annulus fibrosus, becomes weakened through age or injury, it may tear allowing the soft inner part of the disc, the nucleus pulposus, to bulge out. This is called disc herniation, disc prolapse, or a slipped or bulging disc. Once the inner disc material extends out past the regular margin of the outer disc wall, it can press against very sensitive nerve tissue in the spine. The "bulging" disc can compress or even damage the nerve tissue, and this can cause weakness, tingling, or pain in the back area and into one or both legs. The nerve compression can also lead to bowel and bladder dysfunction.

A discectomy is a surgical procedure generally to remove part of an intervertebral disc that is putting pressure on a nerve as it leaves the spinal column. The procedure is most commonly performed on lumbar discs (located in the lower back) creating leg pain. However, it may also be used for cervical discs in the neck.

Open discectomy is usually performed under general anesthesia (the patient is unconscious) and typically requires a one-day hospital stay. It is performed while the patient is lying face down or in a kneeling position. During the procedure, the surgeon will make an approximate one-inch incision in the skin over the affected area of the spine. Muscle tissue is removed from the bone above and below the affected disc and retractors hold the muscle and skin away from the surgical site so the surgeon has a clear view of the vertebrae and disc. In some cases bone and ligaments may have to be removed for the surgeon to be able to visualize and then gain access to the bulging disc without damaging the nerve tissue, this is called a laminectomy or laminotomy depending on how much bone is removed.

Once the surgeon can visualize the vertebrae, disc and other surrounding structures, he or she will remove the section of the disc that is protruding from the disc wall and any other disc fragments that may have been expelled from the disc. This is often done under magnification.

Current discectomy and disc space preparation procedures entail the use of a sharp blade for annulus incision, a Pituitary Rongeur for initial access and removal of a nucleus pulposus, a curette to free up disc material, and a Pituitary Rongeur for disc material removal, a rasp for end plate preparation. Ideally the number of instruments and instrument passes in and out of the disc space should be minimized.

In treating a bulging disc, typically no material is used to replace the disc tissue that is removed. The incision is closed with sutures and the patient is taken to a recovery room. In a disc space preparation procedure, a prosthesis such as a spinal cage is inserted into the disc space upon completion of a partial or complete discectomy. In such a discectomy, enough disc material is removed to enable the deployment of the prosthesis. The opposing vertebral endplate surfaces are cleaned of soft tissue to enable prosthesis attachment or fusion with the vertebral bone tissue.

The most common problem of a discectomy is that there is a chance that another fragment of disc will herniate and cause similar symptoms down the road. This is a so-called recurrent disc herniation, and the risk of this occurring is about 10-15%.

OBJECTS OF THE INVENTION

It is an object of the present invention to provide an improved approach for a disc space preparation procedure.

Another object of the present invention is to provide a surgical disc space preparation procedure that is at least partially quicker, more complete, and easier to carry out than conventional techniques.

Yet another object of the present invention is to provide a surgical disc space preparation procedure that may be performed minimally invasively.

It is a related object of the present invention to provide a surgical discectomy or nucleotomy method, typically as a part of a disc space preparation procedure, that reduces, if not minimizes, the number of instruments and instrument passes in and out of the disc space.

Another related object of the present invention is to provide such a surgical discectomy or nucleotomy method that is at least partially quicker and easier to implement than conventional techniques.

Yet another object of the present invention is to provide such a surgical discectomy or nucleotomy method that may be performed minimally invasively.

These and other objects of the invention will be apparent from the drawings and descriptions herein. Although every object of the invention is attained in at least one embodiment of the invention, there is not necessarily any embodiment which attains all of the objects of the invention.

SUMMARY OF THE INVENTION

The present invention contemplates use of an elongate ultrasonic probe in the form of a symmetric dissector-shaver which includes a shaft and a laterally enlarged head extending distally and transversely from a distal end of the shaft. The head is provided with multiple energy-concentrating projections, exemplarily in the form of knurls or teeth and more preferably sets of spiraling ribs. The energy-concentrating projections may take any form. Two criss-crossing sets of spiraling ribs have been found to be effective, but other configurations of ribs or protuberances can be used.

A spinal surgery method in accordance with the present invention comprises providing an ultrasonic probe including an elongate shaft and a laterally enlarged head at a distal end of the shaft and conducting ultrasonic vibratory energy into the ultrasonic probe to generate a standing wave therein. During the conducting of ultrasonic vibratory energy, a distal end of an ultrasonic probe is inserted into a spinal disc between two vertebral endplates. Thereafter, also during the conducting of ultrasonic vibratory energy, the ultrasonic probe is manipulated to move the laterally enlarged head within the spinal disc to thereby disrupt and shred the spinal disc material into fragments exhibiting a range of different sizes including fragments too large to aspirate from a disc space between the vertebral endplates. The fragments are extracted from the space, in part by using forceps to pull spinal disc fragments from the operative space or surgical site between the vertebral endplates and in part by applying suction. Inasmuch as irrigation is delivered to the surgical site, that is, the disc space, suction removes many small particulates and disc detritus as a slurry. Aspiration may occur simultaneously or alternative with the fragmentation of disc material via the ultrasonic probe. The presence of irrigant enables sonication, that is, the production of smaller fragments via cavitation, thus facilitating disc material removal via aspiration.

The laterally enlarged head of the ultrasonic probe is moved along all three spatial axes, that is, alternately in a distal and a proximal direction, alternately towards left and right, and alternately towards and away from the vertebral end plate surfaces. The last motion repetitively traps or squeezes elastic disc material between the probe head and the endplates, enhancing if not enabling the severing of disk material into fragments. The laterally enlarged head typically and preferably includes an arced perimetral portion that projects beyond distal and proximal portions of the head, and in preferred embodiments constitutes a knurled or toothed edge with a radius of curvature that approximates radii of curvature of the concave vertebral end plate surfaces facing the disc space.

It is to be noted that a disc space preparation procedure as described herein need not remove all of the subject spinal disc. It is necessary to remove only enough disc material to enable installation of a prosthesis such as a rigid cage or a gel-filled sac. For example, the discectomy portion of the disc space preparation procedure may include only the nucleus pulposus or a portion thereof or may also include a portion of the annulus fibrosus. The cleaning of the vertebral end plate surfaces is necessary to enable anchoring or attachment of the prosthesis to the endplates.

Pursuant to another feature of the present invention, the inserting of the distal end of the ultrasonic probe into the spinal disc includes, during the conducting of ultrasonic vibratory energy, manipulating the ultrasonic probe to perform an annulotomy on the spinal disc. The ultrasonic instrument may be used, prior to the inserting of the distal end of the ultrasonic probe into the spinal disc and prior to the manipulating of the ultrasonic probe to perform the annulotomy, to remove osteophytes from one or both of the vertebral endplates. This is particularly necessary in some special cases to enable insertion and deployment of a fusion cage in the disc space.

It is to be noted that the same dissector-shaver instrument may be used to remove osteophytes, perform an annulotomy, perform a discectomy, and clean the vertebral endplate faces of disc material, soft tissue and cartilage. The consequent reduction of the number of instruments required not only facilitates an entire disc space preparation operation but also reduces chances of inadvertent injury to non-target tissues.

Accordingly, the present invention contemplates that the laterally enlarged head includes at last one convexly arcuate edge disposed in a major plane orthogonal to a longitudinal axis of the shaft. This edge preferably has an elongate shape with a curvature or profile matched to or approximating curvatures of a concave vertebral end plate surface, thus facilitating cleaning of the endplate surface of soft tissue after at least substantial removal of the body of the respective spinal disc.

Preferably, the head has two opposed mirror-symmetric convex edge segments disposed in the major plane of the head. During the conducting of ultrasonic vibratory energy into the ultrasonic probe, the probe is manipulated to engage first one and then another of the vertebral endplates with respective ones of the two opposed mirror-symmetric convex edge segments to thereby remove disc material from surfaces of both of the vertebral endplates. The curvatures of the convex edge segments conform generally or approximately to the curvatures of the endplate surfaces, thereby optimizing removal of soft tissue and minimizing the removal of bone tissue from the vertebral endplates.

The laterally enlarged head has its largest transverse dimensions, as measured in the major plane orthogonally to the longitudinal axis of the shaft. Concomitantly, the laterally enlarged head tapers down in a proximal direction from the major plane to the shaft and in a distal direction from the major plane to a free end opposite the shaft.

Pursuant to a feature of the surgical method in accordance with the present invention, the range of disc fragment sizes extends from less than one millimeter to more than one centimeter. Possibly, the disc fragments can be as long as two or three centimeters with a width of a few millimeters. While such large fragments are extracted via a graspers or forceps, smaller, particulate, fragments or particles can be aspirated from the space.

An ultrasonic probe particularly for use in the above-described procedure comprises an elongate shaft, a connector at a proximal end of the shaft for operatively coupling the shaft to a source of ultrasonic vibratory energy to generate a mechanical standing wave in the probe, and a laterally enlarged head at a distal end of the shaft. The laterally enlarged head tapers down in a proximal direction from the major plane to the shaft and in a distal direction from the major plane to a free end of the probe opposite the shaft. The laterally enlarged head includes at least one convexly arcuate edge disposed in a major plane oriented at least approximately orthogonally to a longitudinal axis of the shaft. Preferably the laterally enlarged head is larger in one direction than other directions oriented at an angle thereto in the major plane of the head. In other words, the head is oblate or flattened so as to exhibit, in a transverse cross-section taken in the major plane (and generally in other planes parallel thereto), an oval or longitudinal U.S. football profile.

The at least one convexly arcuate edge is preferably one of two opposed mirror-symmetric convex edge segments disposed in the major plane of the head. The two opposed mirror-symmetric convex edge elements may lie along an ellipse. The convex edge segments may meet in the major plane at opposed vertices or, alternatively, may connect smoothly with one another in arcs of greater curvature (smaller radius of curvature). In the latter case, the laterally enlarged head may include a distal end surface and a proximal end surface each in the form of a cross-sectionally elliptical cone, each of the distal end surface and the proximal end surface being contiguous with both of the two opposed mirror-symmetric convex edge segments.

Preferably the two opposed mirror-symmetric convex edge segments, the distal end surface and the proximal end surface are textured or knurled. The texturing or knurling may be accomplished by forming the distal end surface and the proximal end surface of the probe head with spiraling ribs. The ribs may include two overlapping or intersecting sets of parallel mutually spaced ribs, the ribs of one set oriented in one direction and the ribs of the other set angled in another direction. Other configurations of ribs may be used and other ways of generating the The shaft or the probe is preferably provided with a channel or lumen, advantageously used to convey liquid irrigant or coolant to the operative site. The laterally enlarged head has an aperture on a distal side, the aperture communicating with the channel or lumen. The aperture may have a circular rim, on a distal side of the head, opposite the shaft, which facilitates penetration into disc material when the probe is moved in the distal direction.

In one possible embodiment, the laterally enlarged head has an ellipsoidal or ovoid form, like a football in the American game. The ends of the head may be more or less sharp or pointed and can take the form of spherical sections. The laterally enlarged head includes a distal end surface and a proximal end surface each having an at least approximately elliptical cross-section.

After removal of a spinal disc as described herein, the two vertebral endplates may be fused to one another exemplarily via insertion of a rigid cage that becomes attached to the vertebral endplates. Alternatively, a disc prosthesis or graft may be inserted between the two vertebrae. The ultrasonically vibrating of the head during the contacting of the vertebral endplates serves in part to provide the opposing faces with textured surfaces. The leveling and texturing of the vertebral surfaces opens access to the blood vessels in the vertebrae and facilitates subsequent growth and attachment of the bone to the material of a disc prosthesis or graft.

The channel or lumen in the probe shaft and the aperture in the probe head communicating therewith may be used in part to feed a cooling liquid to the probe head and particularly to knurled surfaces thereof during the contacting of the opposing faces of the vertebrae. In addition, the channel or lumen may be used to aspirate the particulate matter formed during the ultrasonic disruption process. The inserting of the distal end of the probe into the spinal disc includes operating the instrument to form an opening in the annulus of the spinal disc and to penetrate through the opening into the disc.

The aspirating of particulate disc material may occur in part during the generating of the standing wave in the probe. Alternatively, the vibrating of the tool may be momentarily interrupted during the aspiration process. Aspiration and irrigation may be applied in alternation, with the irrigation serving (i) to cool the probe during ultrasonic energization, (ii) to render particulate material into a slurry for extraction via suction and (iii) to dislodge larger fragment than may become wedged into the distal end of the channel or lumen, exemplarily in the probe head.

A suction source, with a particulates trap, and a pressurized irrigant supply may be connected to the channel or lumen of the probe shaft via a manifold with valves actuated, for instance, by at least one foot switch, enabling an operator to vary probe functionality in accordance with exigencies of a surgical procedure A spinal surgical method pursuant to the present invention may rely on and incorporate conventional open surgery or minimally invasive procedures for obtaining access to a target disc space. The surgical method of the present invention proceeds in the same way regardless of the access method used.

A surgical method pursuant to the present invention may be performed manually or in part automatically via computer-guided robotic mechanisms. In addition, whether manually or robotically executed, the method may be carried out with the assistance of navigation system exemplarily including scanners or trackers and associated computer software to image the patient's spinal tissues, for instance, prior to the commencement of surgery, and track the location of the probe during surgery and particularly the probe head within the patient. The probe may be provided, for instance, with X-ray-opaque fiducial markings or one or more radio-frequency transmitters or other location-encoding devices to facilitate computer tracking of probe head location and optionally probe orientation relative to spinal structures, and to enable imaging on a computer monitor of the probe together with and in relation to spinal structures. Exemplary navigation systems include Medtronic's Stealth Station S8 EM Navigation System and Stryker's NAV3i Platform. Such systems can be and are used with a variety of different surgical instruments to track the instruments, enhancing surgical accuracy and increasing patient safety.

DEFINITIONS

The term "discectomy" is used herein to designate a procedure involving removal of spinal disc material from a spinal disc between two vertebrae or vertebral endplates. The disc material being removed may be small, for instance, to prevent impingement of a spinal disc on the spinal cord. Alternatively, a discectomy may entail removal of a substantial portion of a disc, such as the nucleus pulposus, or an entire disc including both the pulposus and the annulus fibrosus.

A "disc space preparation" procedure pursuant to the present disclosure includes not only a substantial discectomy, or removal of a substantial portion or all of a spinal disc, but also contemplates preparation of the adjacent vertebral end faces so that a prosthesis inserted into the disc space between the two vertebral endplates satisfactorily adheres to the endplates. The preparation of the disc space includes cleaning or removal of disc material, soft tissue and cartilage from the vertebral end faces, thereby increasing the likelihood of proper adhesion of a prosthesis to the vertebrae. The cleaning of the endplate faces or surfaces typically results in possibly undesirable but unavoidable removal of osseous tissue. Vertebral osteophytes may be removed in the process. The use of an ultrasonic probe to clean vertebral endplates is advantageous in that little force need be applied to the vertebrae. Thus greater control is possible, enabling a surgeon to remove just enough disc material and cartilage to enable fusion of a prosthesis with the bony tissue, without unnecessarily increasing the chances of the prosthesis breaking through and rupturing the vertebral end face.

The term "probe" or "ultrasonic probe" is used herein to designate an elongate metallic tool designed to carry an ultrasonic standing wave of a predetermined ultrasonic frequency, so that an operative surface or edge at the distal end of the probe entertains a maximal movement amplitude at the predetermined ultrasonic frequency and a correspondingly maximized transmission of ultrasonic vibratory energy to a target organic tissue within a patient.

The term "major plane" is used herein to describe the plane transverse to an ultrasonic probe's longitudinal axis wherein the probe head is widest and thus has its greatest transverse dimension. The probe head preferably has a cutting edge, and more preferably two opposed cutting edges, disposed in the major (transverse) plane.

The term "laterally enlarged" is used herein to describe a probe head that is wider than the distal end of the probe shaft. The probe head projects to the side beyond the shaft, at least in part facilitating contact with vertebral endplate faces.

DETAILED DESCRIPTION

Figure 1:
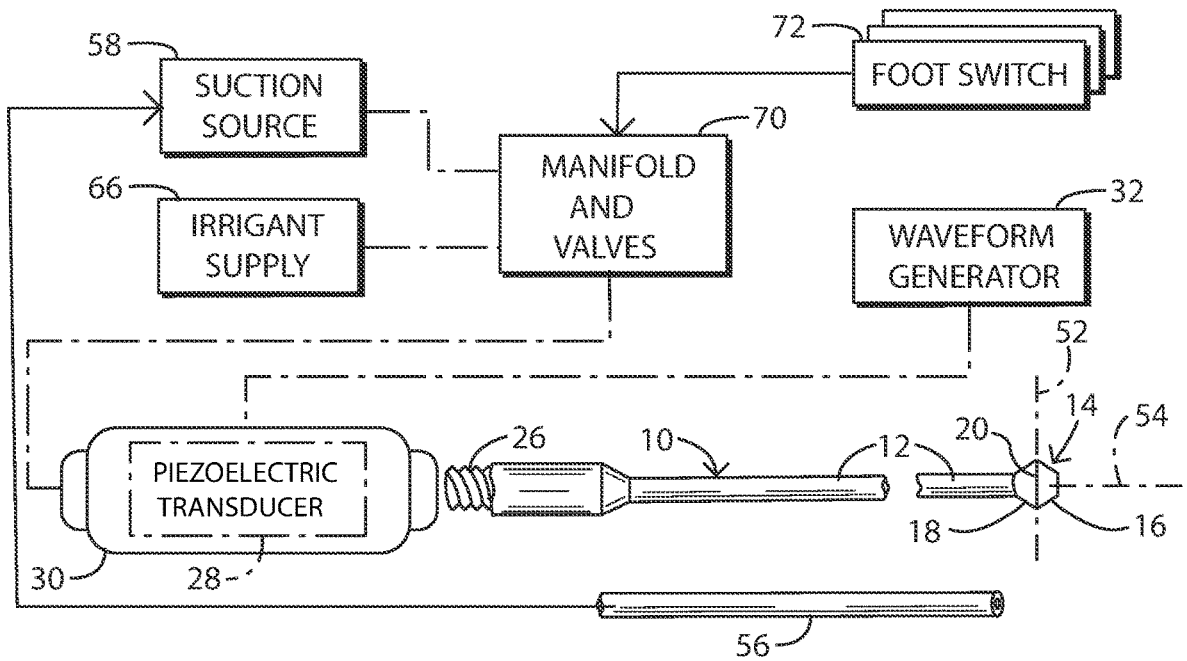
FIG. 1 is partially a schematic side elevational view of an ultrasonic probe and partially a block diagram of ancillary components of a prior art system for use in performing a discectomy or disc space preparation procedure pursuant to the present invention.
Figure 2:
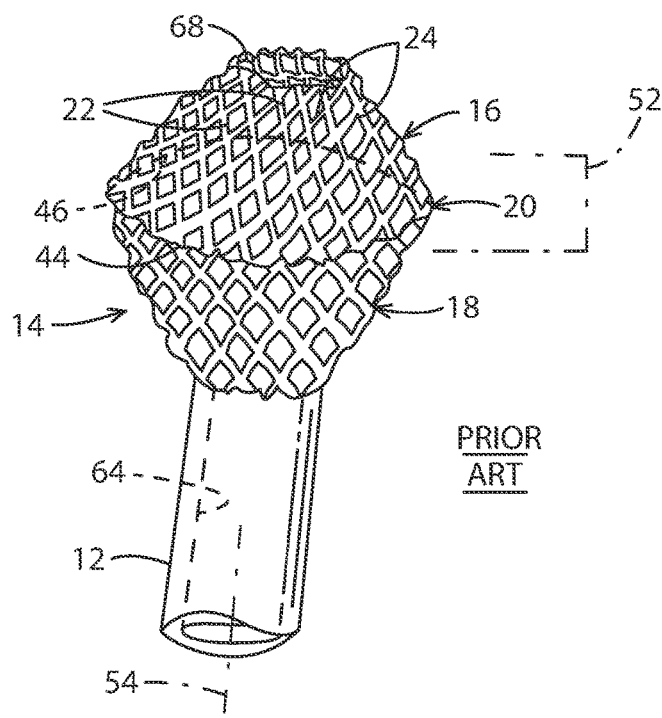
FIG. 2 is a distal end and side perspective view, on a larger scale, of the prior art probe of FIG. 1.

FIGS. 1 and 2 depict an ultrasonic instrument that can be used in a discectomy or disc space preparation procedure. The instrument is an elongate dissector-shaver probe 10 which includes a linear distal shaft section 12 and an axially symmetric head 14 extending both distally and transversely or laterally from a distal end (not separately designated) of the shaft section 12. Head 14 has a conical distal end surface 16 and a conical proximal end surface 18 that join one another along a circular edge 20. Distal end surface 16 and proximal end surface 18 are each provided with energy concentrating projections such as knurls or teeth superimposed on or generated by two sets of spiraling ribs 22 and 24 overlaid on conical walls that define distal end surface 16 and proximal end surface 18. Ribs 22 spiral in one direction and ribs 24 spiral at a different angle so that the ribs 22 and 24 intersect each other to form distal end surface 16 and proximal end surface 18 as networks or webs of diamond or rhombus shapes.

Dissector-shaver probe 10 includes a threaded coupling 26 connectable to a piezoelectric or magnetostrictive transducer 28 in a handle or housing 30 that in turn is operatively connectable to an ultrasonic waveform generator 32. Transducer 28 converts an applied or incoming electrical waveform form generator 32 into a mechanical ultrasonic vibration that produces a standing waveform in probe 10.

Figure 3:
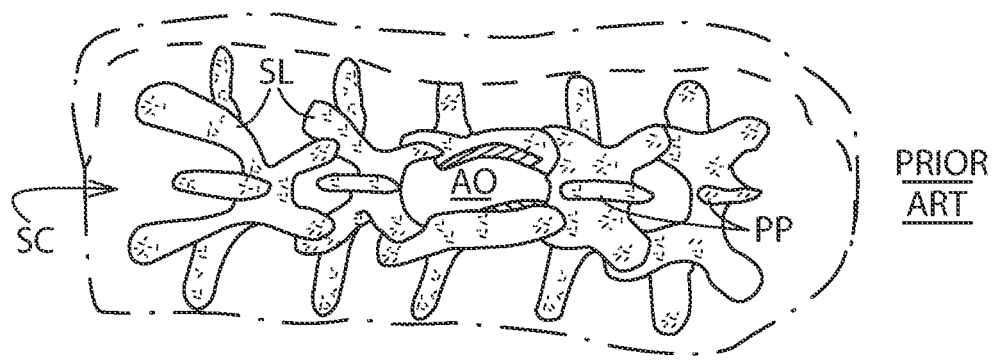
FIG. 3 is a rear elevational view of an anatomical model used heuristically to explain and practice a discectomy or disc space preparation procedure in accordance with the present invention.

As shown in FIG. 3, a spinal column SC includes a series of spinal bone elements including spinous processes PP and laminae SL spaced from each other in a linear array. FIG. 3 depicts a step in an open-surgery discectomy or disc space preparation procedure, wherein a spinal process and associated lamina have been removed from spinal column SC to create an opening AO enabling access to a target spinal disc SD (FIGS. 4-7) and adjacent vertebral endplates V1 and V2 (FIGS. 4 and 6).

Figure 4:
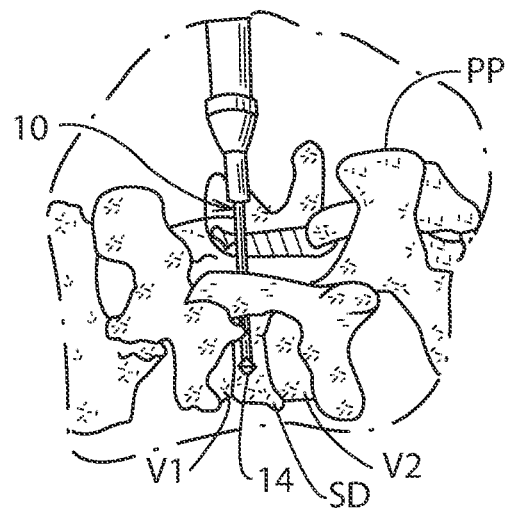
FIG. 4 is a side elevational view of the model of FIG. 3, showing the ultrasonic probe of FIGS. 1 and 2 placed alongside a spinal disc in the model of FIG. 3 to illustrate the surgical method pursuant to the present invention.
Figure 7:
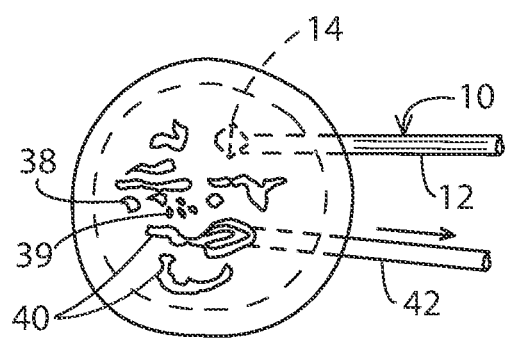
FIG. 7 is a schematic top plan view similar to FIG. 5, showing additional steps in the surgical method pursuant to the present invention.
Figure 5:
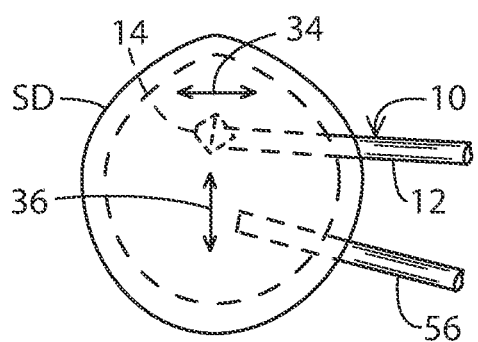
FIG. 5 is a schematic top or bottom plan view of a spinal disc, illustrating steps in the surgical method pursuant to the present invention.
Figure 6:
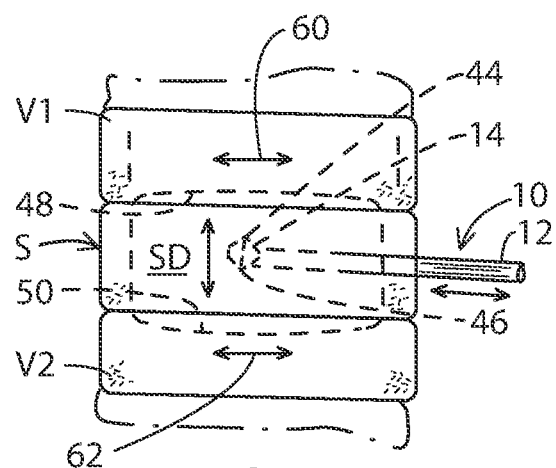
FIG. 6 is a schematic side-elevational view of the spinal disc of FIG. 5 and adjacent or flanking vertebral endplates, depicting further steps in the surgical method pursuant to the present invention.

As illustrated in FIGS. 4-6, a surgical discectomy or disc space preparation procedure entails inserting head 14 (or any of the heads disclosed herein with reference to FIGS. 8-12) and a distal end portion of shaft 12 into a spinal disc SD in a direction generally parallel to vertebral endplates V1 and V2 adjacent to the spinal disc. During the inserting of probe 10, waveform generator 32 and transducer 28 ultrasonically vibrate the probe. Thereafter, while probe 10 continues to ultrasonically vibrate, one manipulates the probe via handle or housing 30 to move the surgical head 14 alternately in a distal and a proximal direction (away from and towards the surgeon), as indicated by a double-headed arrow 34, and alternately towards the left and the right within the spinal disc SD, as indicated by a double headed arrow 36. This generally repetitive but selectively variable motion disrupts and shreds the material of spinal disc SD into fragments 38, 39, 40 (FIG. 7) exhibiting a range of different sizes including fragments 40 too large to aspirate from a disc space S between vertebral endplates V1 and V2 (see FIG. 6). Fragments 40 are extracted from space S by using a graspers or forceps 42 (FIG. 7) such as a Pituitary Rongeurs to pull the fragments from the operative space or surgical site S.

Circular edge 20 of head 14 includes a pair of opposed convexly arcuate edge segments 44 and 46 that face major surfaces 48 and 50 of respective vertebral endplates V1 and V2. Circular edge 20 and accordingly convexly arcuate edge segments 44 and 46 lie in and define a major plane 52 of head 14 oriented orthogonally to a longitudinal axis 54 of shaft 12. The term "major plane" is used herein to designate a plane in which head 14 (114, 214, 314, 414) has a larger cross-section than in all other planes parallel to the major plane. Flattened probe heads typically have one major plane perpendicular to the longitudinal axis of the probe and another major plane containing the probe or shaft axis.

After extraction of the disrupted disc SD or a substantial portion thereof, in part through pulling of large disc fragments 40 out from space S by graspers 42 and in part through aspiration of particulate spinal disc material 39 by means of a suction cannula 56 connected to a suction source 58 (FIG. 1), probe 10 is manipulated to move edge segments 44 and 46 along respective surfaces 48 and 50 of vertebral endplates V1 and V2, as indicated by double-headed arrows 60 and 62 in FIG. 6, to clear disc material from the endplates and roughen the same in preparation for deployment of an intervertebral prosthesis.

Figure 8:
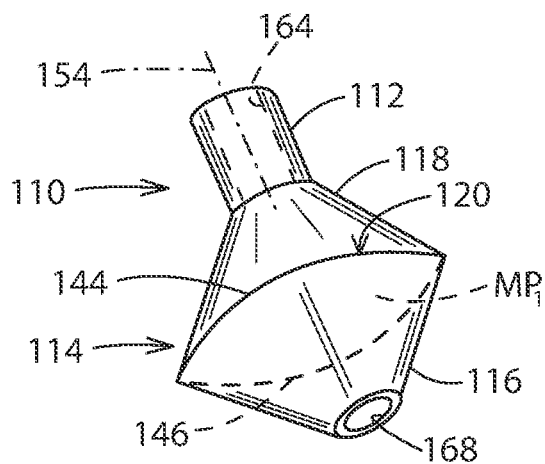
FIG. 8 is a schematic perspective view, on an enlarged scale, of a distal end portion of an ultrasonic surgical probe or instrument in accordance with the present invention for use in a surgical procedure pursuant to the invention.
Figure 9:
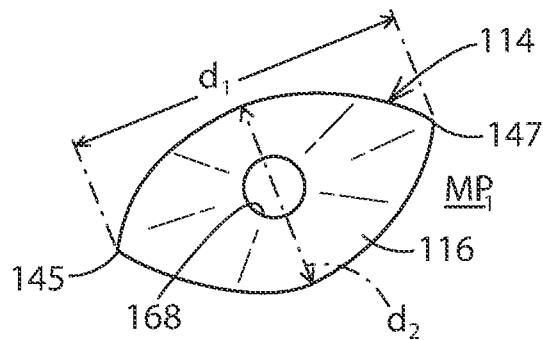
FIG. 9 is a schematic front elevational view of the ultrasonic surgical probe of FIG. 8, taken from the distal end of the instrument.

Probe 10 works efficaciously in disrupting, shredding and tearing apart the material of spinal disc SD. While probe head 14 functions tolerably well in cleaning and roughening surfaces 48 and 50 of vertebral endplates V1 and V2, a different geometry is optimal for that purpose. FIGS. 8 and 9 depict a probe 110 with a shaft 112 and a laterally enlarged head 114 that has a maximum transverse dimension d1 in along one direction in a major plane $MP_1$ (parallel to the plane of the paper in FIG. 9) oriented perpendicularly to a longitudinal axis 154 of probe shaft 112. Head 114 intersects plane $MP_1$ along a pair of elongated convexly arcuate edge segments 144 and 146 contiguous with one another at sharp vertices or rounded apices 145 and 147. Like head 14, head 114 tapers down in both a distal direction towards a free end and in a proximal direction towards the respective shaft 112. More specifically, head 114 exhibits a laterally distorted conical distal end surface 116 and a laterally distorted conical proximal end surface 118, each flattened in one transverse direction and stretched in another transverse direction, that join one another along a generally oval edge 120 comprising elongated convexly arcuate edge segments 144 and 146 and rounded apices 145 and 147. Like surfaces 16 and 18 of head 14, distal end surface 116 and proximal end surface 118 are each provided with knurls or teeth particularly in the form of two sets of energy-concentrating spiraling ribs (not illustrated) extending at an acute angle relative to one another to form end surfaces 116 and 118 as networks or webs of diamond or rhombus shapes and to knurl arcuate edge segments 144 and 146 and rounded apices 145 and 147. It is to be understood that energy concentrating projections on the probe heads disclosed herein extend outwardly to a greater height than the remaining outer areas of the heads, particularly including the spiraling ribs.

Arcuate edge segments 144 and 146 are optimally elongated to fit along concave vertebral end plate surfaces 48 and 50, matching curvatures thereof, thus facilitating cleaning of the endplate surfaces after at least substantial removal of the body of the respective spinal disc SD as described hereinabove. Edge segments 144 and 146 constitute two opposed mirror-symmetric knurled abrading edges disposed in major plane $MP_1$ of head 114. During the conducting of ultrasonic vibratory energy into the ultrasonic probe 110, the probe is manipulated to engage first one and then another of the vertebral endplates V1, V2 with edge segments 144, 146, respectively, with probe 110 being moved alternately back and forth along the vertebral surfaces 48 and 50 in a distal and proximal direction as indicated by arrows 60 and 62 in FIG. 6, to thereby remove disc material from surfaces 48 and 50. The curvatures of the convex edge segments 144 and 146 conform generally or approximately to the curvatures of the endplate surfaces 48 and 50, thereby minimizing the removal of bone tissue, as opposed to disc material, from the vertebral endplates V1 and V2.

Figure 10:
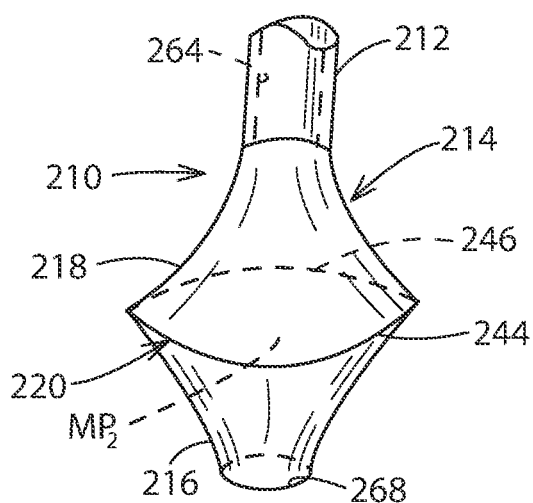
FIG. 10 is a schematic perspective view, on an enlarged scale, of a distal end portion of another ultrasonic surgical probe or instrument in accordance with the present invention for use in a surgical procedure pursuant to the invention.

Head 114 has its largest transverse dimensions $d_1$ and $d_2$ in the major plane MP', respectively along a major axis and a minor axis (not separately designated) both orthogonal to the longitudinal axis 154 of shaft 112. Edges 20 and 120 of probe heads 14 and 114 are formed as intersections or joints between two surfaces 44, 46 and 144, 146 of different inclinations. FIG. 10 shows a probe 210 with a laterally enlarged head 214 having a distal end surface 216 and a proximal end surface 218 that intersect to form an oval cutting edge 220, where end surfaces 216 and 218 are concave facing outwardly rather than linearly sloped like quasi-conical surfaces 116 and 118. Oval cutting edge 220 is disposed in and defines a transversely oriented major plane $MP_2$ of head 214.

Figure 11:
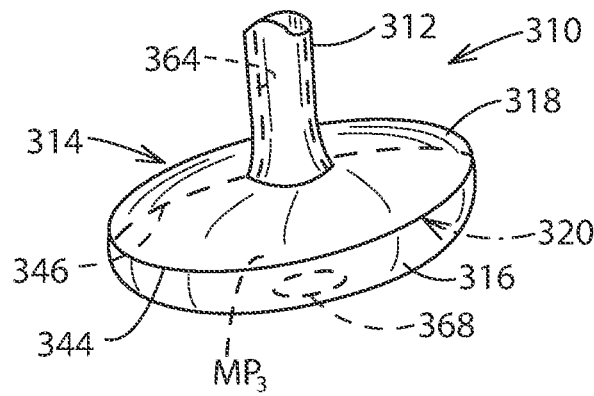
FIG. 11 is a schematic perspective view, on an enlarged scale, of a distal end portion of a further ultrasonic surgical probe or instrument in accordance with the present invention for use in a surgical procedure pursuant to the invention.

FIG. 11 depicts a probe 310 with a laterally enlarged head 314 having a distal end surface 316 and a proximal end surface 318 that intersect to form an oval cutting edge 320, where end surfaces 316 and 318 are convex facing outwardly rather than concave or linearly sloped. Oval cutting edge 320 is disposed in and defines a transversely oriented major plane $MP_3$ of head 314.

Heads 214 and 314 are both oblate or flattened in a direction transverse to respective shaft axes 254 and 354. Thus each head 214 and 314, like head 114, exhibits an oval or elliptical transverse cross-section in all planes perpendicular to the respective longitudinal shaft axis 254, 354. Each such laterally enlarged head 114, 214, 314 tapers down in a proximal direction from the plane of the respective oval edge 120, 220, 320 to the respective shaft 112, 212, 312 and in a distal direction from the oval edge to a free end opposite the shaft.

Figure 12:
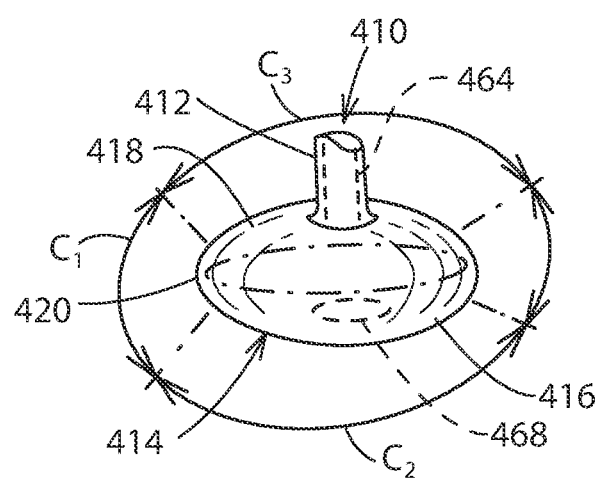
FIG. 12 is a schematic perspective view, on an enlarged scale, of a distal end portion of yet another ultrasonic surgical probe or instrument in accordance with the present invention for use in a surgical procedure pursuant to the invention.

FIG. 12 depicts a probe 410 with a shaft 412 and a laterally enlarged head 414 having an ellipsoidal distal end surface 416 and an ellipsoidal proximal end surface 418 that are joined to one another by a blunt annular edge or transversely outermost surface 420 of greater curvature $C_1$ (smaller radius of curvature) than curvatures $C_2$ and $C_3$ of end surfaces 416 and 418. Edge surface 420 exemplarily has a circular shape seen in an axial plane. Probe 410 is useful in performing a partial discectomy such as a nucleotomy or a disc space preparation procedure including the performing of a partial discectomy. Head 414 may take on an ellipsoidal form, tracing an arc of an ellipse of revolution. Outermost surface 420 is bisected by and concomitantly defines a transverse major plane $MP_4$ of head 414.

The present invention mainly contemplates that shafts 12, 112, 212, 312, 412 are formed with respective channels or lumens 64, 164, 264, 364, 464 that communicate with a pressurized supply 66 (FIG. 1) of cooling liquid or irrigant. The irrigant is typically conducted through the channels or lumens 64, 164, 264, 364, 464 from supply 66 during an ultrasonic surgical procedure and particularly during the energization of the probes 10, 110, 210, 310, 410 with ultrasonic mechanical vibratory energy generated by transducer 28 in response to an electrical waveform from generator 32. The irrigant exits the head 14, 114, 214, 314, 414 through an aperture 68, 168, 268, 368, 468 at a distal or free end of the head and optionally through one or more apertures (not shown) provided in distal end portion 16, 116, 216, 316, 416 and/or proximal end portion 18, 118, 218, 318, 418 between intersecting spiraling ribs 22 and 24 (FIG. 2). Heads 114, 214, 314, 414 are all preferably formed as network of intersecting spiraling ribs 22 and 24 (FIG. 2). The irrigant serves in part to maintain the instrument and the tissues at thermal equilibrium during ultrasonic energization of the probe within the patient. The irrigant also serves to enable ultrasonic cavitation and to generate a slurry of disc and endplate surface particulates that may be extracted via aspiration.

Disc fragments 38, 39, 40 have sizes in a range from less than one millimeter to more than one centimeter. The larger disc fragments 40 can be as long as two or three centimeters with a width of a few millimeters. While such large fragments are extracted via graspers or forceps 42, smaller, particulate, fragments or particles 39 can be aspirated from the surgical site or operative space S by suction source 58 via cannula 56.

Edges 120, 220, 320 each incorporate two opposed mirror-symmetric convex edge segments 144, 146 and 244, 246, and 344, 346 disposed in the major plane of the head 114, 214, 314. The two opposed mirror-symmetric convex edge elements 144, 146 and 244, 246, and 344, 346 may each lie along an ellipse. Where the two opposed mirror-symmetric convex edge elements 144, 146 and 244, 246, and 344, 346 both lie along the same ellipse, the respective distal end surface 116, 216, 316 and proximal end surface 118, 218, 318 each take the form of a truncated cross-sectionally elliptical cone, each distal end surface and proximal end surface being contiguous with both of the two opposed mirror-symmetric convex edge segments 144, 146 and 244, 246, and 344, 346.

After removal of spinal disc SD as described above, vertebral endplates V1 and V2 may be fused to one another. Alternatively, a disc prosthesis or graft may be inserted between the two vertebrae V1, V2. The ultrasonically vibrating of the head 14, 114, 214, 314, 414 during the contacting of the vertebral endplates V1, V2 (arrows 60, 62) serves in part to provide the opposing faces 48, 50 with textured surfaces free of disc material and cartilaginous tissue. The leveling and texturing of the vertebral surfaces opens access to the blood vessels in the vertebrae and facilitates subsequent growth and attachment of the bone to the material of a disc prosthesis or graft.

Channel or lumen 64, 164, 264, 364, 464 and aperture 68, 168, 268, 368, 468 in probe head 14, 114, 214, 314, 414 communicating therewith are used to convey irrigant to the probe head and to ambient or adjacent tissues during the contacting of the opposing faces 48, 50 of the vertebral endplates V1, V2. In addition, on some occasions, it may be advantageous to use the channel or lumen 64, 164, 264, 364, 464 to aspirate particulate matter 39 formed during the ultrasonic disruption process. The aspirating of particulate disc material either by cannula 56 or probe 10, 110, 210, 310, 410 may occur in part during the generating of the standing wave in the probe. Alternatively, the vibrating of the tool may be momentarily interrupted during the aspiration process. Aspiration and irrigation may be applied in alternation, with the irrigation serving (i) to cool the probe during ultrasonic energization, (ii) to render particulate material into a slurry for extraction via suction and (iii) to dislodge larger fragment than may become wedged into the distal end of the channel or lumen, exemplarily in the probe head.

Suction source 58 includes a particulates trap and supplies irrigant under pressure to channel or lumen 64, 164, 264, 364, 464 via a manifold 70 (FIG. 1) with valves actuated, for instance, by at least one foot switch 72, enabling an operator to vary probe functionality in accordance with exigencies of a surgical procedure A spinal surgical method pursuant to the present invention may rely on and incorporate conventional open surgery or minimally invasive procedures for obtaining access to a target disc space. The surgical method of the present invention proceeds in the same way regardless of the access method used. In addition, the present invention may be used together with robotics and existing navigation systems to facilitate control of instrument movements relative to patient tissue structures. The navigation systems include scanners or trackers and associated computer software that may be used to record 3D structural data of a patient's spinal tissues prior to surgery. The systems track the locations of surgical instruments during surgery and particularly the locations of end effectors or operative tips of the instruments within the patients. A probe may be provided with fiducial markings or electromagnetic wave transmitters or other location-encoding devices to facilitate computer tracking of probe head location and optionally probe orientation relative to spinal structures, and to enable imaging on a computer monitor of the probe together with and in relation to spinal structures. Exemplary navigation systems include Medtronic's Stealth Station S8 EM Navigation System and Stryker's NAV3i Platform. Such systems can be and are used with a variety of different surgical instruments to track the instruments, enhancing surgical accuracy and increasing patient safety.

The invention effectuates disc disruption and fragmentation primarily through mechanical action of the probe through the disc material. Disc material is highly elastic and frequently impervious to ultrasonic ablation. However, the present method combines the application of ultrasonic vibratory energy with larger-scale mechanical motion that provides a radically improvement over ultrasound and large scale mechanical motion individually. The trapping of disc material between the probe head and a vertebral endplate facilitates selective disruption of elastic disc material. A secondary means of disc fragmentation provided by the present invention is ultrasonic cavitation or sonication, which is made possible with the introduction of liquid irrigant into the disc space. A further technique comprises irradiating a target disc with radio-frequency electromagnetic energy prior to and during the energization and movement of the ultrasonic probe within the disc and/or along the vertebral endplate faces. The radiation reduces the elasticity of the disc material and improves disc fragmentation and vertebral cleaning.

It is to be noted that an ultrasonic probe 12, 112, 212, 312, 412 as disclosed herein provides tactile feedback so that the operating surgeon can sense immediately when the probe head 14, 114, 214, 314, 414 comes into contact with a surface of a vertebral endplate V1, V2. This feedback prompts a change in force application and possibly direction of probe movement and facilitates cleaning of the endplate surfaces without unduly abrading and ablating bony tissue from the endplates V1, V2.

A set of surgical instruments peculiar to the disc space preparation procedure described herein may be combined as a kit, including dissector shaver 12, 112, 212, 312, and/or 412, one or more suction cannulas 56, and one or more graspers or forceps 42. These may be packaged together in a single container or otherwise sold together.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof

What is claimed is:
1. A spinal surgery method comprising:
   providing an ultrasonic probe including an elongate shaft and a laterally enlarged head at a distal end of said shaft;
   conducting ultrasonic vibratory energy into said ultrasonic probe to generate a standing wave therein;
   during the conducting of ultrasonic vibratory energy, inserting a distal end of an ultrasonic probe into a spinal disc between two vertebral endplates;
   thereafter, also during the conducting of ultrasonic vibratory energy, manipulating said ultrasonic probe to move said laterally enlarged head alternately in a distal and a proximal direction, alternately towards left and right within said spinal disc, and alternately towards and away from the vertebral end plate surfaces to thereby disrupt and shred at least a portion of said spinal disc into fragments exhibiting a range of different sizes including segments too large to aspirate from a space occupied by said spinal disc between said vertebral endplates; and extracting said fragments from said space, the extracting of said fragments including using forceps or graspers to pull at least some of said segments from said space.

2. The spinal surgery method defined in claim 1 wherein said laterally enlarged head includes at least one convexly arcuate edge disposed in a major plane orthogonal to a longitudinal axis of said shaft, said laterally enlarged head having largest dimensions orthogonal to said longitudinal axis located in said major plane, said laterally enlarged head tapering down in a proximal direction from said major plane to said shaft, said laterally enlarged head tapering down in a distal direction from said major plane to a free end opposite said shaft.

3. The spinal surgery method defined in claim 2 wherein said at least one convexly arcuate edge is one of two opposed mirror-symmetric convex edge segments disposed in said major plane, further comprising, during the conducting of ultrasonic vibratory energy, manipulating said ultrasonic probe to engage first one and then another of said vertebral endplates with respective ones of said two opposed mirror-symmetric convex edge segments to thereby remove disc material from surfaces of both of said vertebral endplates.

4. The spinal surgery method defined in claim 2, further comprising, during the conducting of ultrasonic vibratory energy, manipulating said ultrasonic probe to engage at least one of said vertebral endplates with said at least one convexly arcuate edge to thereby remove disc material from a surface of said at least one of said vertebral endplates facing said space.

5. The spinal surgery method defined in claim 1 wherein the inserting of the distal end of the ultrasonic probe into the spinal disc includes, during the conducting of ultrasonic vibratory energy, manipulating the ultrasonic probe to perform an annulotomy on the spinal disc.

6. The spinal surgery method defined in claim 5, further comprising operating an ultrasonic instrument, prior to the inserting of the distal end of the ultrasonic probe into the spinal disc and prior to the manipulating of the ultrasonic probe to perform the annulotomy, using said ultrasonic instrument to remove osteophytes from one or both of the vertebral endplates.

7. The spinal surgery method defined in claim 1 wherein the manipulating of said ultrasonic probe includes manipulating said ultrasonic probe to move said laterally enlarged head alternately towards and away from one of said vertebral endplates so as to trap disc material between said laterally enlarged probe head and said one of said vertebral endplates, whereby the trapped disc material is severed.

8. The spinal surgery method defined in claim 1, further comprising, during the conducting of ultrasonic vibratory energy, manipulating said ultrasonic probe to engage said vertebral endplates with said laterally enlarged head and thereby remove disc material soft tissue and cartilage from surfaces of said vertebral endplates.

9. The spinal surgery method defined in claim 1 wherein said range extends from less than one millimeter to more than one centimeter.

10. The spinal surgery method defined in claim 1 wherein the extracting of said fragments includes aspirating some of said fragments from said space.

11. The spinal surgery method defined in claim 1 wherein said forceps is a Pituitary Rongeurs.

* * * * *